United States Patent
Fruchey

(10) Patent No.: US 8,685,253 B2
(45) Date of Patent: Apr. 1, 2014

(54) PROCESSES FOR REMOVING COLOR DURING PRODUCTION OF RUNWAY DEICER

(75) Inventor: Olan S. Fruchey, Hurricane, WV (US)

(73) Assignee: BioAmber S.A.S. (FR)

( * ) Notice: Subject to any disclaimer, the term of this patent is extended or adjusted under 35 U.S.C. 154(b) by 465 days.

(21) Appl. No.: 12/889,599

(22) Filed: Sep. 24, 2010

(65) Prior Publication Data

US 2011/0089364 A1    Apr. 21, 2011

Related U.S. Application Data

(60) Provisional application No. 61/247,419, filed on Sep. 30, 2009.

(51) Int. Cl.
*B01D 21/00* (2006.01)
*C02F 1/52* (2006.01)
*B03D 3/00* (2006.01)
*C02F 1/72* (2006.01)
*C02F 103/28* (2006.01)

(52) U.S. Cl.
CPC ............. *C02F 1/722* (2013.01); *C02F 1/5236* (2013.01); *C02F 2103/28* (2013.01); *Y10S 210/917* (2013.01)
USPC ........... 210/724; 210/917; 210/759; 210/758; 210/723; 210/721

(58) Field of Classification Search
USPC ......... 210/723, 724, 758, 759, 639, 638, 917, 210/702, 721; 435/136, 137
See application file for complete search history.

(56) References Cited

U.S. PATENT DOCUMENTS

| | | | |
|---|---|---|---|
| 2,013,096 A | | 9/1935 | Haag |
| 3,736,254 A | * | 5/1973 | Croom .......................... 210/724 |
| 5,302,288 A | * | 4/1994 | Meidl et al. .................. 210/616 |
| 5,681,728 A | * | 10/1997 | Miao ............................. 435/136 |
| 5,814,498 A | * | 9/1998 | Mani et al. .................... 435/136 |
| 2006/0276674 A1 | * | 12/2006 | Kushiku et al. ............... 562/562 |

FOREIGN PATENT DOCUMENTS

| | | | | |
|---|---|---|---|---|
| CN | 101 348 428 | | 1/2009 | |
| GB | 416483 | * | 9/1934 | ............... C02F 5/02 |
| JP | 2006-280274 A | | 10/2006 | |
| JP | 2007-060972 A | | 3/2007 | |
| KR | 10-0466385 B1 | | 1/2005 | |
| KR | 10-0483693 B1 | | 4/2005 | |
| KR | 10-0811615 B1 | | 3/2008 | |
| WO | 2007/086864 A2 | | 8/2007 | |

OTHER PUBLICATIONS

Wu, S. et al., "Downstream Processing of Pullulan from Fermentation Broth," *Carbohydrate Polymers*, 2009, vol. 77, pp. 750-753.

* cited by examiner

*Primary Examiner* — Nam Nguyen
*Assistant Examiner* — Nader Hossaini
(74) *Attorney, Agent, or Firm* — DLA Piper LLP (US)

(57) ABSTRACT

A method of removing color bodies from a fermentation broth includes precipitating a color-forming impurity (color body) by adjusting the fermentation broth to a pH greater than about 13; filtering our precipitated color-forming impurities from the broth; and bleaching a second color impurity by treating the broth with an oxidizing agent.

12 Claims, No Drawings

PROCESSES FOR REMOVING COLOR DURING PRODUCTION OF RUNWAY DEICER

RELATED APPLICATION

This application claims the benefit of U.S. Provisional Application No. 61/247,419, filed Sep. 30, 2009. This earlier provisional application is hereby incorporated by reference.

TECHNICAL FIELD

This disclosure relates to processes for removing color bodies during production of runway deicer.

BACKGROUND

Biocatalytic processes such as those using numerous fermentable sugars as a substrate are seen as an economical and environmental alternative to traditional petrochemical processes. Biocatalytic processes involving conversion of low value carbohydrates, including agricultural and forestry waste, is of increasing interest due to the depletion of fossil derived hydrocarbon feedstocks used in petrochemical processes.

Succinic acid (SA) can be produced by microorganisms using fermentable sugars as a starting material. Most succinate producing microorganisms require neutralization of the fermentation broth to maintain an appropriate pH for maximum growth, conversion and productivity. Consequently, salts of SA such as monoammonium succinate (MAS) and diammonium succinate (DAS) are obtained by conversion of carbohydrates in the broth in the presence of succinate producing microorganisms. A cation elimination process is necessary to obtain the acid, wherein the base cation needed to neutralize the acid in the fermentation is replaced by protonation with a mineral acid such as sulfuric or electrodialysis. Conversion of the salt to the acid and its purification involve several unit operations that could potentially diminish the economic viability of biobased SA as a raw material for the production of runway deicers.

The runway deicer of interest is an aqueous mixed salt solution of dipotassium succinate/potassium acetate/potassium formate. Aqueous mixed salts of disodium succinate/sodium acetate/sodium formate are also of interest. It is thus desirable to prepare the salt solution directly from the fermentation broth, without isolating and purifying the SA.

It could therefore be helpful to provide for economical production of a runway deicer from a fermentation mixture without first either separating and purifying SA or a succinate salt from the numerous impurities and particularly color bodies present in the fermentation broth.

SUMMARY

I provide a method of removing color bodies from a fermentation broth which includes precipitating a color-forming impurity (color body) by adjusting the fermentation broth to a pH greater than about 13; filtering out precipitated color-forming impurities from the broth; and bleaching a second color impurity by treating the broth with an oxidizing agent.

I also provide a method of removing color bodies from a fermentation both containing DAS, MAS or mixtures thereof including precipitating a color body by adjusting the fermentation broth to a pH greater that about 13; filtering out the precipitated color body from the broth; and bleaching a second color body by treating the broth with an oxidizing agent.

I further provide a process for producing a runway deicer including clarifying an ammonium succinate fermentation broth by ultrafiltration; concentrating the broth by reverse osmosis, precipitating out a color body by adjusting pH of the broth to greater than about 13 with potassium hydroxide; filtering out the precipitated color body from the both; concentrating the resulting potassium succinate solution by evaporating a portion of water and most ammonia in the solution; adding hydrogen peroxide to the solution to further lighten the residue; and adjusting the pH to about 10.5 by adding an acid.

DETAILED DESCRIPTION

It will be appreciated that the following description is intended to refer to specific examples described herein and is not intended to define or limit the disclosure, other than in the appended claims.

Microorganisms capable of producing SA from carbohydrate sugars include, but are not limited to, *Escherichia coli* or *E. coli, Aspergillus niger, Corynebacterium glutamicum* (also called *Brevibacterium flavum*), *Enterococcus faecalis, Veillonella parvula, Actinobacillus succinogenes, Mannheimia succiniciproducens, Anaerobiospirillum succiniciproducens, Paecilomyces Varioti, Saccharomyces cerevisiae, Bacteroides fragilis, Bacteroides ruminicola, Bacteroides amylophilus, Alcaligenes eutrophus, Brevibacterium ammoniagenes, Brevibacterium lactofermentum, Candida brumptii, Candida catenulate, Candida mycoderma, Candida zeylanoides, Candida paludigena, Candida sonorensis, Candida utilis, Candida zeylanoides, Debaryomyces hansenii, Fusarium oxysporum, Humicola lanuginosa, Kloeckera apiculata, Kluyveromyces lactis, Kluyveromyces wickerhamii, Penicillium simplicissimum, Pichia anomala, Pichia besseyi, Pichia media, Pichia guilliermondii, Pichia inositovora, Pichia stipidis, Saccharomyces bayantis, Schizosaccharomyces pombe, Torulopsis candida* and *Yarrowia lipolytica*.

Dipotassium succinate (DPS) is produced from a fermentation-derived DAS broth. This broth contains color-forming impurities that must be removed during production. If not removed, these substances yield a very dark brown runway deicer product. Removal of these impurities by these processes yields a light yellow product which can be readily dyed blue (the color required for runway deicers). The processes extend to color removal from other bio-derived mono, di, and tri carboxylic and hydroxylcarboxylic acids (for example, acetic, lactic, citric, malonic and adipic acids) and aminoacids.

DAS generated by fermentation of biomass is contained in a dilute aqueous solution also containing fermentation byproducts and trace color-forming impurities. Reaction of the crude fermentation broth with potassium hydroxide converts it directly into a dilute aqueous solution of DPS with dissolved ammonia. Distillation of the reaction mixture removes the ammonia and a portion of the water yielding a concentrated aqueous DPS solution (~35-50%) which also contains some potassium acetate and potassium formate. The resulting solution is dark brown (yellowness index of ~25) due to the concentration of the color-forming impurities present in the fermentation broth. This material cannot be effectively dyed blue for final product use.

SA is a diprotic acid with pKa1 and pKa2 being equal to 4.19 and 5.48, respectively. As is typical for polyprotic acids, the protons are lost consecutively. When reacting with a base, the first proton is removed from the molecules of SA, forming a half acid/half salt before the second proton is lost from the half acid/half salt. In the case of SA, the first proton comes from an acid stronger than acetic acid (pKa 4.74) and the second proton comes from an acid weaker than acetic acid.

SA can be produced by a fermentation process using fermentable sugars as the starting material. Most commercially viable, succinate producing micro-organisms described in the literature require neutralization of the fermentation broth to maintain an appropriate pH for maximum growth, conversion and productivity. Therefore, a salt of SA is obtained from the fermentation reactor. Typically ammonium salts of SA (DAS, MAS or mixtures thereof) are obtained. Thus, the fermentation is conducted with a continual addition of aqueous ammonia (ammonium hydroxide) based on pH control (see EQ-1):

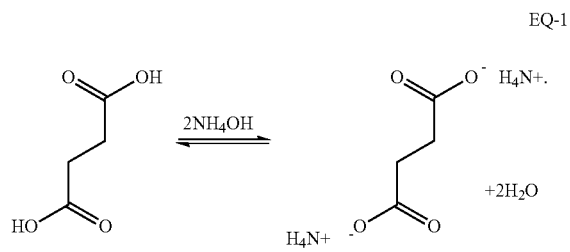

EQ-1

The broth from the fermentation reactor typically has a concentration of about 2 to about 10% DAS, MAS or mixtures thereof. The broth also contains several other impurities (e.g., ammonium acetate, ammonium lactate, ammonium formate and ammonium pyruvate) as well as insoluble cell bodies and unknown color bodies. These cell bodies can be removed by crossflow or other suitable filtration methods, yielding a clarified broth. The broth can then be concentrated to about 4 to about 15% DAS, MAS or mixtures thereof using a reverse osmosis membrane. The reverse osmosis membrane removes water leaving the salts behind and is thus a low energy way of concentrating the broth.

When the clarified and concentrated solution is reacted with a 45% potassium hydroxide solution it yields a 5-18% DPS solution which is saturated with dissolved ammonia (see EQ-2):

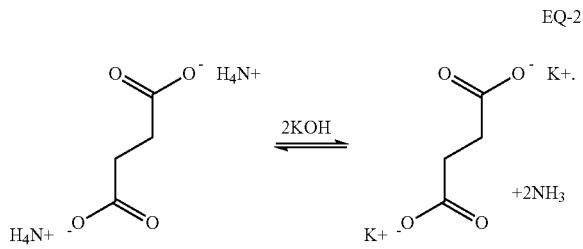

EQ-2

This solution has a strong ammonia odor and slowly loses ammonia to the atmosphere upon standing in an open vessel. The dissolved ammonia can also be removed from the solution by heating or vacuum. In fact, when the temperature of the solution reaches about 95° C. at atmospheric pressure, the ammonia is rapidly lost from the solution along with some water. The ammonia is not condensed in the evaporator, but rather absorbed into the condensed water on the cooling surface of the condenser. This means that the distillate from the evaporator is an aqueous ammonia solution which can be recycled to the fermentation reactor for pH control.

The fermentation broth has a pH of about 5 to about 8 and, upon addition of the potassium hydroxide, the pH will rise to greater than about 11. The pH of pure DPS is nearly neutral (about 7.5). However, the presence of the potassium salts from the other acids (e.g., acetic acid) causes the pH of the solution to increase to about 8.5 in the absence of dissolved ammonia. The high pH observed upon potassium hydroxide addition to a DAS/MAS solution is due to the dissolved ammonia. Stripping off the ammonia lowers the pH to that of the pure salts. However, if excess potassium hydroxide is added, the final pH is greater than the pH of the pure salts. The target pH for the final solution is about 10.5, which means excess potassium hydroxide relative to the stoichiometric amount should be added. It is preferable to have excess potassium hydroxide present during the evaporation step so that very little ammonia is left. If an insufficient amount of potassium hydroxide is added before the evaporation step, then unreleased ammonia is left in solution as ammonium ions which are liberated upon post evaporation pH adjustment. Excess potassium hydroxide (above the amount required for final pH) can be neutralized by addition of acetic acid or formic acid after the evaporation step without the potential to release ammonia. The acetic acid reacts with the potassium hydroxide forming potassium acetate (see EQ-3). The analogous reaction occurs with formic acid. If excess acetic acid is added during the pH adjustment, it can be back-neutralized with potassium hydroxide.

$$KOH + HOAc \rightarrow KOAc + H_2O \qquad \text{EQ-3}$$

The DAS/MAS fermentation broth contains color-forming impurities that yield a dark brown solution when treated with potassium hydroxide and concentrated to an about 35-about 50% DPS solution. (Synthetic solutions of about 35-about 50% DPS are colorless.) The resulting dark brown DPS solution (obtained from broth-based DAS/MAS) is not acceptable for addition of the blue dye required for the final product. A typical yellowness index (YI) for broth-based about 40% DPS solutions is about 25. It has been estimated that the about 40% DPS solution should have a YI of less than about 6 to give acceptable treatment with the dye. The color can be decreased by treating with reducing agents such as sodium hydrosulfite and sodium borohydride prior to evaporation. Also, a carbon treatment in conjunction with sodium hydrosulfite produces faintly yellow solutions with an acceptable YI. Unfortunately, these pretreated solutions turn brown after standing for several weeks.

It appears that the impurities in the broth that impart the brown color to the solution are present in the broth feed initially and the color intensification observed for the final solution is a result of a simple concentration increase during the evaporation step. These impurities, when reacted with reducing agent (e.g., sodium hydrosulfite, also known as sodium dithionite) and heated for evaporation, are readily converted into species having much lower color intensity. Unfortunately, it appears that these reduced species can reoxidize to the colored species during storage. It is likely that the reoxidation results from the dissolved oxygen in the solutions. The identity of the color-forming impurities is not known because they are probably present in very low ppm levels. However, it appears that the color-formers can be interconverted between the highly colored oxidized species and the low color reduced species. This is evident by the fact that color can be reduced again by the addition of sodium hydrosulfite to samples that had developed color upon standing.

The color-formers in the DAS broth appear to behave similarly to the redox cycle that has been established for paraaminophenol (PAP). When PAP (colorless solution) is oxidized, it forms the highly colored quinonimine. The quinonimine can be reduced back to PAP with sodium hydrosulfite and the PAP can then again be oxidized to the quinonimine in a repeatable cycle. This type of redox cycle is also known to occur for hydroquinone (HQ). When HQ (a colorless solution) is oxidized, it forms the dark colored parabenzoquinone (PBQ). The PBQ can then be reduced to HQ and the cycle continued. For both of these examples cited, the oxidation is typically accomplished via dissolved oxygen in the aqueous solution. It is not implied that the color-forming impurity in the fermentation-derived DAS/MAS is either PAP or HQ analogs, only that it is a species that is capable of a redox cycle.

Surprisingly, we found that this brown redox cycle impurity can be precipitated from solution by adjusting the pH of the clarified and reverse osmosis concentrated broth to about 13.4 (target pH range about 13.0 to about 13.7). If this high pH solution is allowed to stand for about 60 minutes, a dark colored flocculant material settles to the bottom of the container. This flocculant material can be separated from solution by standard methods such as filtration through a pad of celite (filter aid) or the like.

The yellow filtrate then contains only an impurity that responds to oxidation. Reducible color-forming impurities have been removed. The yellow color can be further lightened if necessary by treatment with an oxidizing agent such as hydrogen peroxide.

The final product (about 40% DPS solution) is dyed blue before it is sold as a runway deicer. Therefore, the about 35-about 50% solution should not be highly colored. In fact, tests have shown that the final product should not have a yellowness index greater than about 6. If the yellowness index is greater than about 6, then it cannot be effectively dyed.

DPS-containing fermentation broth contains color-forming impurities that cause the yellowness index of the final product to be about 25 (a dark brown solution) if not treated. There are at least two different color-formers in the broth that use two separate treatments. The first color-former can be precipitated from solution by adjusting the RO-concentrated broth to pH of about 13.4 (range about 13.0 to about 13.7). The pH is adjusted by adding excess KOH during the reaction step. The solution should be held (either stagnant or stirred) for about 1 hour at this pH. During this hold time, a very small amount of fine brown solids precipitates from solution, but stays suspended if stirred. These brown solids can be removed by standard separation techniques such as a vacuum or pressure filtration with a pad of celite (i.e., filter aid) or the like. The filtration step yields a yellow solution that can then be fed to the evaporator for concentration to about 35-50% dipotassium succinate.

After the evaporation step, the concentrated residue is still too dark (YI about 9-about 15) for dye treatment. The second color-former can then be bleached by treatment with an oxidizing agent such as hydrogen peroxide at high pH and at room temperature. Aqueous hydrogen peroxide (about 3500 ppm of contained hydrogen peroxide relative to the contained DPS) is added to the cooled residue and allowed to stand with stirring for about 16 hours. During this hold time, the solution becomes very light yellow (YI about 4). If the broth batch has more color-forming impurities than normal, one can increase the hydrogen peroxide level to achieve the desired final color. After the desired color is achieved, then the pH can be adjusted (to about 10.5) by adding formic acid and/or acetic acid to meet final product specifications.

It is preferable to perform the hydrogen peroxide treatment while the solution pH is still above about 13. If the pH is adjusted to about 10.5 before addition of the hydrogen peroxide, then lower level color removal is observed. Furthermore, the hydrogen peroxide treatment works best at around room temperature (~25° C.) and is less effective at higher temperatures. This temperature effect probably results from thermal degradation of the hydrogen peroxide at higher temperatures.

In summary, the color treatment process may be two steps: 1) a high-pH precipitation performed before the evaporation step, and 2) a hydrogen peroxide bleaching step performed after the evaporation step. It is possible to perform both steps simultaneously prior to evaporation (i.e., add KOH and then add hydrogen peroxide followed by stirring, e.g., one hour, and filtration). It is also possible to do the KOH precipitation and hydrogen peroxide steps sequentially before the evaporation step (i.e., treat with KOH and filter, then treat the filtrate with hydrogen peroxide).

Any alkaline or alkali base may be used in place of KOH such as sodium hydroxide, for example. Furthermore, other oxidizing agents may be used in place of the hydrogen peroxide oxidant (i.e., ozone, oxygen or the like could be used as the oxidizing agent). Quantities may vary depending on the level of color-forming impurities in the solution being treated.

I thus provide methods that incorporate base-promoted precipitation of a color body by adjusting the solution to a high pH (typically greater than about pH 13) followed by filtration to remove one type of color-forming impurity, followed by addition of an oxidizing agent to remove a second type of color-forming impurity.

The process may comprise:
1. precipitation of a color body by adjusting pH of the fermentation broth to greater than about 13 by addition of a strong base;
2. filtering out the precipitated color body;
3. concentrating the solution by evaporation of a portion of the water and most of the ammonia; and
4. addition of an oxidizing agent to further lighten the evaporation residue.

The process for producing a fermentation-derived succinate deicer may comprise:
1. clarification of an ammonium succinate fermentation broth by ultrafiltration;
2. concentration of the clarified broth by reverse osmosis;
3. precipitating out a color body by adjusting pH of the concentrated broth to greater than about 13 with potassium hydroxide;
4. filtering out the precipitated color body;
5. concentrating the potassium succinate solution by evaporating a portion of water and most ammonia;
6. addition of hydrogen peroxide to further lighten the residue; and
7. adjusting the pH to about 10.5 by addition of an acid.

My processes are demonstrated, but not limited by the following examples.

Example 1

A 4-L beaker was charged with 1500 g of reverse osmosis-concentrated DAS broth (~9.5% DAS). Then 260 g of 45% KOH solution was added slowly while stirring. The pH was next adjusted to 13.4 with 53 g of 45% KOH solution. The contents of the beaker were allowed to stir for 1 hour. At the end of the 1-hour period, the contents were filtered by pumping through a pressure filter that had been precharged with a pad of celite filter aid. A 1-L three neck round bottom flask was charged with 800 g of the filtrate. The flask was fitted with a distillation head and an addition funnel. The addition funnel was charged with 100 g of filtrate. The flask was heated with a heating mantle and stirred with a magnetic stirrer to initiate distillation. After 100 g of distillate was collected, the 100 g of filtrate in the addition funnel was slowly added. This was repeated until all of the filtrate in the filter funnel had been added to the flask through the addition funnel. The distillation was continued until a total of 1370 g of distillate had been collected, yielding 398 g of residue. The flask contents were cooled to room temperature and then 20 g of 3% hydrogen peroxide was added to the flask. The flask contents were then allowed to stir for 16 hours. After the 16 hours, 14.3 g of formic acid and 2 g of acetic acid were added to the flask. The contents were transferred to a 1-L beaker and the pH (10.5) measured. The contents were then allowed to stir for 4 hours and finally filtered through filter paper to remove particulate material. This yielded 386 g of light yellow product (yellowness index 5).

Example 2

A 1-L beaker was charged with 509 g of reverse osmosis-concentrated DAS broth (~9.5% diammonium succinate). The pH was then adjusted to 13.4 by addition of 45% KOH solution. After standing for one hour, the contents were vacuum filtered through a pad of celite filter aid. A 400 g portion of the filtrate was placed in a 1-L round bottom flask and 5 g of 3% hydrogen peroxide added. The contents were allowed to stir for one hour and then the flask was fitted with a distillation head. The flask was then heated with a heating mantle and stirred with a magnetic stirrer to initiate distillation. The distillation was stopped after 305 g of distillate were collected. The residue (91.5 g) had a yellowness index of 5 and contained 38.5% DAS.

Example 3

A 2-L beaker was charged with 800 g of reverse osmosis-concentrated DAS broth (~9.5% DAS). The pH was adjusted to 13.4 by adding 134 g of 45% KOH solution. After stirring for 1 hour, the contents were vacuum filtered through a pad of celite filter aid. The filtrate was placed in a 1-L round bottom flask equipped with a distillation head. The flask was then heated with a heating mantle and stirred with a magnetic stirrer to initiate distillation. The distillation was stopped after 688 g of distillate were collected. The residue (209 g) was filtered to remove suspended solids, yield a light brown liquid with a yellowness index of 16, containing 39% DPS.

Example 4

A 40 g sample of the residue from Example 3 was placed in a beaker with 2 g of 3% hydrogen peroxide solution and allowed to stir overnight. The next day the yellowness index of the residue was measured as 3.

Example 5

This example demonstrates the conversion of pure DAS to DPS. To 373 g of water was added 30.5 g of SA and 31.5 g of concentrated (14.8 N) ammonium hydroxide. To this solution of DAS was then slowly added 65 g of 45% potassium hydroxide solution. A clean 250 mL round bottom flask containing a stir bar was then fitted with a Dean Stark trap topped with a reflux condenser. The flask was then fitted with a thermometer to read the pot temperature. The flask was charged with 100.3 g of the above prepared diammonium succinate solution. The contents of the flask were heated with an oil bath and 78.3 g of distillate was collected in the Dean Stark trap. The pot temperature as the last drop distilled over was 114° C. The cooled colorless residue (18.3 g) was discharged from the pot. Analyses of the residue revealed a 55.3% DPS concentration and a pH of 7.7.

Comparative Example 1

This example demonstrates the reaction of potassium hydroxide with a fermentation broth containing color-forming impurities and ammonium slats, without our color reduction process. To 1000 g of fermentation broth containing 4.6% DAS, 0.5% ammonium acetate, 0.04% ammonium lactate and 0.02% ammonium formate was added 87 g of 45% potassium hydroxide solution. The resulting pH was 11.0. A clean 500 mL round bottom flask containing a stir bar was then fitted with a Dean Stark trap topped with a reflux condenser. The flask was then fitted with a thermometer to read the pot temperature. The flask was charged with 200 g of the above prepared broth solution. The contents of the flask were heated with an oil bath and 160.2 g of distillate was collected in the Dean Stark trap. The pot temperature as the last drop distilled over was 105° C. The cooled dark brown (yellowness index ~25) residue (35.2 g) was discharged from the pot. Analyses of the residue revealed a 31.3% DPS concentration and a pH of 8.6.

Although my processes have been described in connection with specific forms thereof, it will be appreciated that a wide variety of equivalents may be substituted for the specified elements/steps described herein without departing from the spirit and scope of this disclosure as described in the appended claims.

The invention claimed is:

1. A method of removing color-forming impurities from an aqueous fermentation broth containing carboxylic acids and salts thereof comprising:
    (a) precipitating a first color-forming impurity by adjusting the aqueous fermentation broth containing carboxylic acids and salts thereof to a pH greater than about 13;
    (b) filtering out the precipitated first color-forming impurity from the broth; and
    (c) bleaching a second color impurity by treating the fermentation broth with an oxidizing agent to render a solution comprising carboxylic acids and salts thereof.

2. The method of claim 1, wherein the pH is adjusted by adding an alkali or alkaline base.

3. The method of claim 1, wherein the pH is adjusted by adding potassium hydroxide or sodium hydroxide.

4. The method of claim 1, wherein the oxidizing agent is hydrogen peroxide.

5. The method of claim 1, further comprising:
    before step (c), concentrating the broth by evaporating a portion of water and ammonia present in the broth.

6. The method of claim 1, wherein the solution has a yellowness index of 6 or less.

7. A method of removing color-forming impurities from a fermentation broth containing diammonium succinate, monoammonium succinate or mixtures thereof comprising:
    (a) precipitating a first color-forming impurity by adjusting the fermentation broth to a pH greater than about 13;
    (b) filtering out the precipitated first color-forming impurity from the broth; and
    (c) bleaching a second color impurity by treating the broth with an oxidizing agent to render a solution comprising diammonium succinate monoammonium succinate or mixtures thereof.

8. The method of claim 7, wherein the pH is adjusted by adding an alkali or alkaline base.

9. The method of claim 7, wherein the pH is adjusted by adding potassium hydroxide or sodium hydroxide.

10. The method of claim 7, wherein the oxidizing agent is hydrogen peroxide.

11. The method of claim 7, further comprising:
   before step (c), concentrating the broth by evaporation of a portion of water and ammonia present in the broth.

12. The method of claim 7, wherein the solution has a yellowness index less than about 6.

* * * * *